US008147405B2

(12) United States Patent
Widenhouse et al.

(10) Patent No.: US 8,147,405 B2
(45) Date of Patent: Apr. 3, 2012

(54) SURGICAL ACCESS PORT WITH MULTILAYERED TORTUOUS PATH SEAL

(75) Inventors: Christopher W. Widenhouse, Clarksville, OH (US); Frederick E. Shelton, IV, Hillsboro, OH (US); Chris Cicenas, Pataskala, OH (US); Michael D. Cronin, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 508 days.

(21) Appl. No.: 12/261,672

(22) Filed: Oct. 30, 2008

(65) Prior Publication Data

US 2010/0113882 A1 May 6, 2010

(51) Int. Cl.
*A61B 1/00* (2006.01)
(52) U.S. Cl. .......................................... 600/184
(58) Field of Classification Search .............. 606/213, 606/108, 191–200, 185; 604/264, 506, 164.01; 251/142, 153–156; 600/201–246; 220/745, 220/747, 254.1–254.2, 254.5, 374, 229, 359.3, 220/372; 215/232
See application file for complete search history.

(56) References Cited

U.S. PATENT DOCUMENTS

| | | | | |
|---|---|---|---|---|
| 1,946,363 A * | 2/1934 | Herbert | ............ | 400/210 |
| 3,066,017 A * | 11/1962 | Jahnig | ............ | 422/145 |
| 4,331,254 A * | 5/1982 | Haggerty | ............ | 220/229 |
| 5,111,946 A * | 5/1992 | Glanz | ............ | 215/247 |
| 5,176,652 A * | 1/1993 | Littrell | ............ | 604/167.04 |
| 5,281,199 A * | 1/1994 | Ensminger et al. | ...... | 604/288.03 |
| 5,375,588 A * | 12/1994 | Yoon | ............ | 600/114 |
| 5,480,410 A | 1/1996 | Cuschieri et al. | | |
| 5,514,133 A | 5/1996 | Golub et al. | | |
| 5,524,644 A | 6/1996 | Crook | | |
| 5,640,977 A | 6/1997 | Leahy et al. | | |
| 5,647,855 A * | 7/1997 | Trooskin | ............ | 604/175 |
| 5,649,550 A | 7/1997 | Crook | | |
| 5,813,409 A | 9/1998 | Leahy et al. | | |
| 5,853,395 A | 12/1998 | Crook et al. | | |
| 5,906,577 A | 5/1999 | Beane et al. | | |
| 6,033,426 A | 3/2000 | Kaji | | |
| 6,142,936 A | 11/2000 | Beane et al. | | |
| 6,254,534 B1 | 7/2001 | Butler et al. | | |
| 6,440,063 B1 | 8/2002 | Beane et al. | | |
| 6,450,983 B1 | 9/2002 | Rambo | | |
| 6,578,577 B2 | 6/2003 | Bonadio et al. | | |
| 6,582,364 B2 | 6/2003 | Butler et al. | | |
| 6,846,287 B2 | 1/2005 | Bonadio et al. | | |
| 6,887,194 B2 | 5/2005 | Hart et al. | | |
| 6,908,430 B2 | 6/2005 | Caldwell et al. | | |
| 6,958,037 B2 | 10/2005 | Ewers et al. | | |
| 7,081,106 B1 * | 7/2006 | Guo et al. | ............ | 604/167.06 |
| 7,563,250 B2 * | 7/2009 | Wenchell | ............ | 604/167.01 |
| 2002/0068923 A1 | 6/2002 | Caldwell et al. | | |
| 2002/0097793 A1 | 7/2002 | Struhsaker et al. | | |
| 2002/0183594 A1 | 12/2002 | Beane et al. | | |
| 2003/0004482 A1 * | 1/2003 | Drevik et al. | ............ | 604/378 |

(Continued)

FOREIGN PATENT DOCUMENTS

EP  1135070 B1  9/2004

(Continued)

*Primary Examiner* — Gary Jackson
*Assistant Examiner* — Amy Shipley (57) ABSTRACT

A surgical access device includes a wound protector and an instrument seal. The instrument seal comprises a plurality of resilient membranes each having a plurality of parallel slits. The membranes are stacked relative one another to create a tortuous path preventing insufflatory gases from escaping through the instrument seal.

16 Claims, 9 Drawing Sheets

U.S. PATENT DOCUMENTS

| | | | |
|---|---|---|---|
| 2004/0015185 A1 | 1/2004 | Ewers et al. | |
| 2004/0049099 A1 | 3/2004 | Ewers et al. | |
| 2004/0097793 A1 | 5/2004 | Butler et al. | |
| 2004/0127772 A1 | 7/2004 | Ewers et al. | |
| 2004/0154624 A1 | 8/2004 | Bonadio et al. | |
| 2004/0254426 A1 | 12/2004 | Wenchell | |
| 2004/0267096 A1 | 12/2004 | Caldwell et al. | |
| 2005/0020884 A1 | 1/2005 | Hart et al. | |
| 2005/0096695 A1* | 5/2005 | Olich | 606/213 |
| 2006/0027290 A1* | 2/2006 | Iguchi et al. | 148/241 |
| 2006/0247678 A1* | 11/2006 | Weisenburgh et al. | 606/205 |
| 2008/0210691 A1* | 9/2008 | Yoshinari et al. | 220/560.03 |
| 2009/0270817 A1* | 10/2009 | Moreno et al. | 604/264 |
| 2009/0287060 A1* | 11/2009 | Pell et al. | 600/201 |
| 2010/0049148 A1* | 2/2010 | Siniaguine | 604/308 |
| 2010/0261972 A1* | 10/2010 | Widenhouse et al. | 600/206 |

FOREIGN PATENT DOCUMENTS

| | | |
|---|---|---|
| EP | 1312318 B1 | 12/2005 |
| WO | WO 95/24864 A1 | 9/1995 |
| WO | WO 98/48724 A1 | 11/1998 |
| WO | WO 00/32116 A1 | 6/2000 |
| WO | WO 00/54676 A1 | 9/2000 |
| WO | WO 00/54677 A1 | 9/2000 |
| WO | WO 01/26558 A1 | 4/2001 |
| WO | WO 02/34108 A2 | 5/2002 |
| WO | WO 2004/030547 A1 | 4/2004 |
| WO | WO 2004/054456 A1 | 7/2004 |
| WO | WO 2004/096012 A2 | 11/2004 |
| WO | WO 2005/097019 A2 | 10/2005 |
| WO | WO 2005/097234 A2 | 10/2005 |

* cited by examiner

SURGICAL ACCESS PORT WITH MULTILAYERED TORTUOUS PATH SEAL

BACKGROUND

The present invention relates in general to surgical devices and procedures, and more particularly to access devices.

Surgical procedures are often used to treat and cure a wide range of diseases, conditions, and injuries. Surgery often requires access to internal tissue through open surgical procedures or endoscopic surgical procedures. The term "endoscopic" refers to all types of minimally invasive surgical procedures including laparoscopic and arthroscopic procedures. Endoscopic surgery has numerous advantages compared to traditional open surgical procedures, including reduced trauma, faster recovery, reduced risk of infection, and reduced scarring. Endoscopic surgery is often performed with an insufflatory fluid present within the body cavity, such as carbon dioxide or saline, to provide adequate space to perform the intended surgical procedures. The insufflated cavity is generally under pressure and is sometimes referred to as being in a state of pneumoperitoneum. Surgical access devices are often used to facilitate surgical manipulation of internal tissue while maintaining pneumoperitoneum. For example, trocars are often used to provide a port through which endoscopic surgical instruments are passed. Trocars generally have a sealing valve that prevent the insufflatory fluid from escaping while an instrument is positioned in the trocar. As a further example, hand access ports are also used during endoscopic surgery, sometimes referred to as hand assisted laparoscopic surgery ("HALS"). A hand access port will typically seal around a surgeon's hand or arm to prevent the insufflatory fluid from escaping while allowing the surgeon to manipulate tissue within the patient's body.

While surgical access devices are known, no one has previously made or used a surgical access device in accordance with the present invention.

BRIEF DESCRIPTION OF DRAWINGS

While the specification concludes with claims which particularly point out and distinctly claim the invention, it is believed the invention will be better understood from the following description taken in conjunction with the accompanying drawings illustrating some non-limiting examples of the invention. Unless otherwise indicated, the figures are not necessarily drawn to scale, but rather to illustrate the principles of the invention.

DETAILED DESCRIPTION

FIGS. 1-4 illustrate an example of a surgical access device. The device includes a wound protector (10) and an access port (20). The wound protector (10) in this example is a flexible fixed length type of wound protector. Naturally, other types of known wound protectors may also be used, including without limitation flexible roll-up wound protectors, flexible variable length pull-up types of wound protectors, rigid cannulas, and the like. As an example of use in abdominal surgery, the wound protector (10) could be placed in an incision in the abdominal wall such that the distal ring (12) is adjacent the peritoneal surface and the proximal ring (16) is adjacent the cutaneous surface. The proximal and distal rings (12, 16) are laterally disposed relative the incision to define a flanges (13) that facilitate holding the wound protector (10) in the incision. In this embodiment the proximal ring (16) and distal ring (12) are circular; however, non-circular rings are also possible. In this embodiment the sleeve (14) is a single layered tube of resilient material; however, a discontinuous sleeve or multi-layered sleeves are also possible. The sleeve (14) may be transparent, translucent, or opaque. As shown here, the sleeve (14) is fastened at its ends to the proximal and distal rings (16, 12) using an adhesive or heat sealing techniques; however, alternative techniques may also be employed. The length and diameter of the sleeve (14) can also vary depending upon the intended use. For instance, the sleeve may be between 1 cm and 6 cm in length and between 1 cm and 10 cm in diameter; however, other lengths and diameters are also possible. The thickness of the sleeve (14) can also vary.

Figure 16:
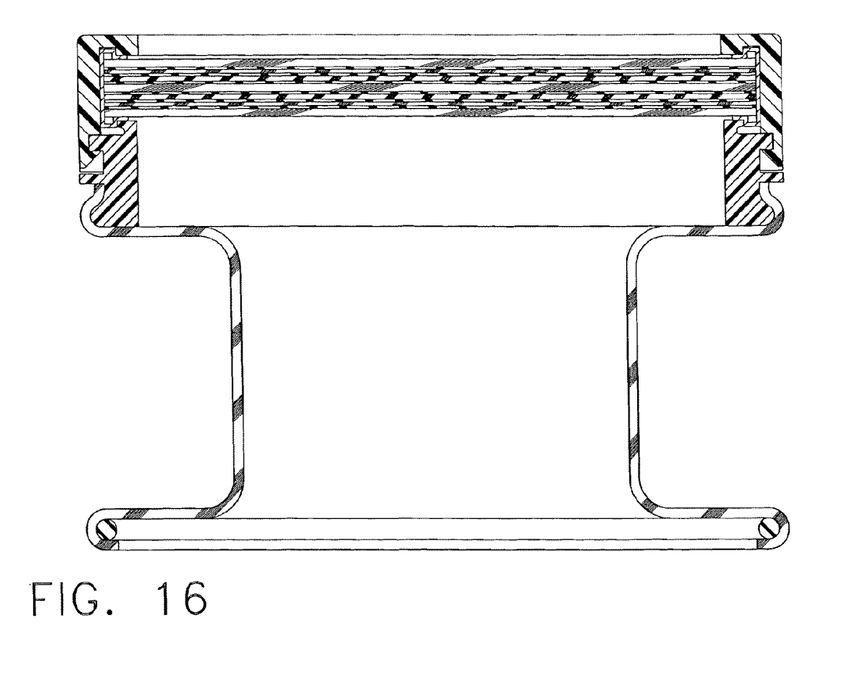
FIG. 16 depicts a cross-sectional view of a multilayered seal.

The retaining ring (22) attaches to the proximal ring (16) to compress and retain therebetween a multilayered seal (24). In this embodiment the seal (24) comprises a plurality of membranes (26) made from a resilient material such as polyurethane-based elastomer, polyester-based elastomer, polyolefin-based elastomer, polyamide-based elastomer, silicone rubber, latex rubber, synthetic isoprene rubber, fluoropolymer based elastomers, and the like. Without limitation, the thickness of the membranes (26) may be are between about 0.5 mm and about 1.5 mm. In this embodiment the membranes (26) each have the same thickness, but membrane (26) thicknesses may varies within the seal (24) such as the embodiment shown in FIG. 16. As shown in FIGS. 1-4, this seal (24) has nine membranes (26), but greater or fewer may also be used. Each membrane (24) is substantially flat and circular with a continuous periphery (27) circumscribing a plurality of parallel elongate slits (28). In one embodiment each membrane (26) may have at least 10 slits (28); however, fewer slits (28) are also contemplated. Without limitation, the area circumscribed by periphery (27) may be between about 6 cm$^2$ and about 200 cm$^2$, and more preferably between about 10 cm$^2$ and about 50 cm$^2$. Without limitation, the distance between the parallel slits (28) may be about 0.5 mm and about 5 mm. As shown in this embodiment, in the resting position (i.e., the absence of a force acting on the slit (28) such as an object being positioned in a slit (28) or a pressure differential across the membrane (24)), the slit (28) remains substantially closed; namely, the edges of the slit (28) are closely adjacent one another. The membranes (26) are stacked upon one another such that the slits (28) of a given membrane (26) are substantially perpendicular to the slits (28) of the adjacent membranes (26).

Figure 1:
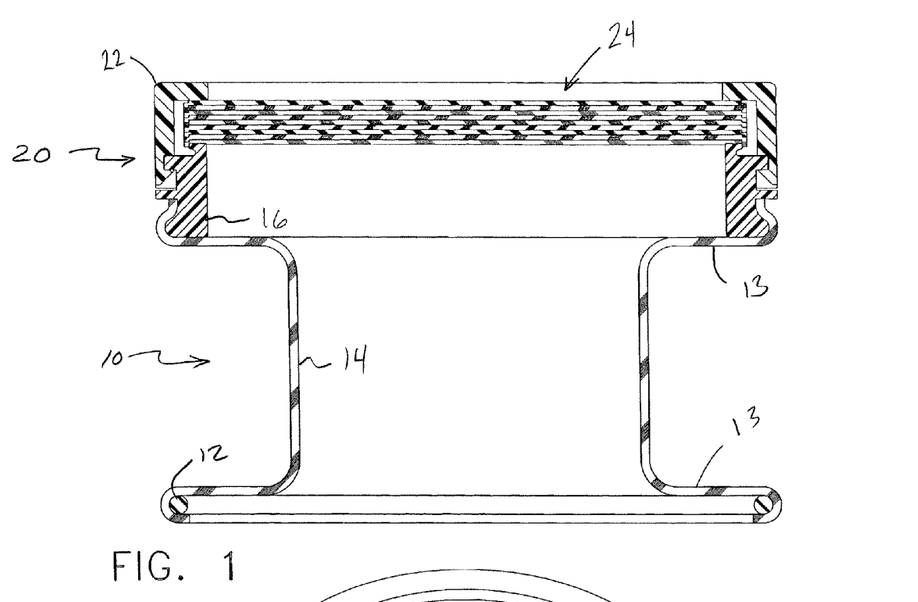
FIG. 1 depicts an cross-sectional view of an access device with a multilayered seal.
Figure 2:
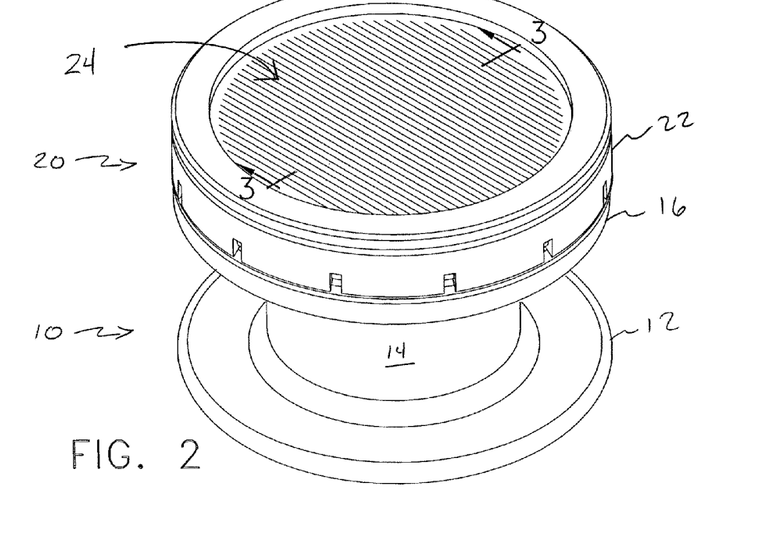
FIG. 2 depicts a perspective view of the access device of FIG. 1.
Figure 3:
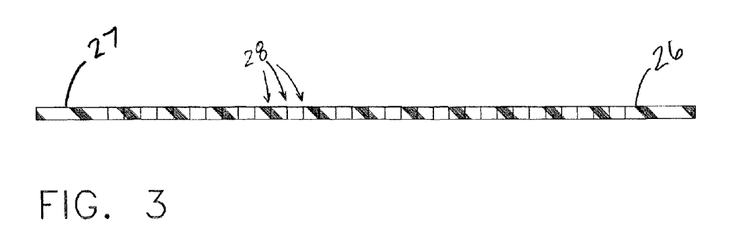
FIG. 3 depicts a cross-sectional view of a seal layer.
Figure 4:
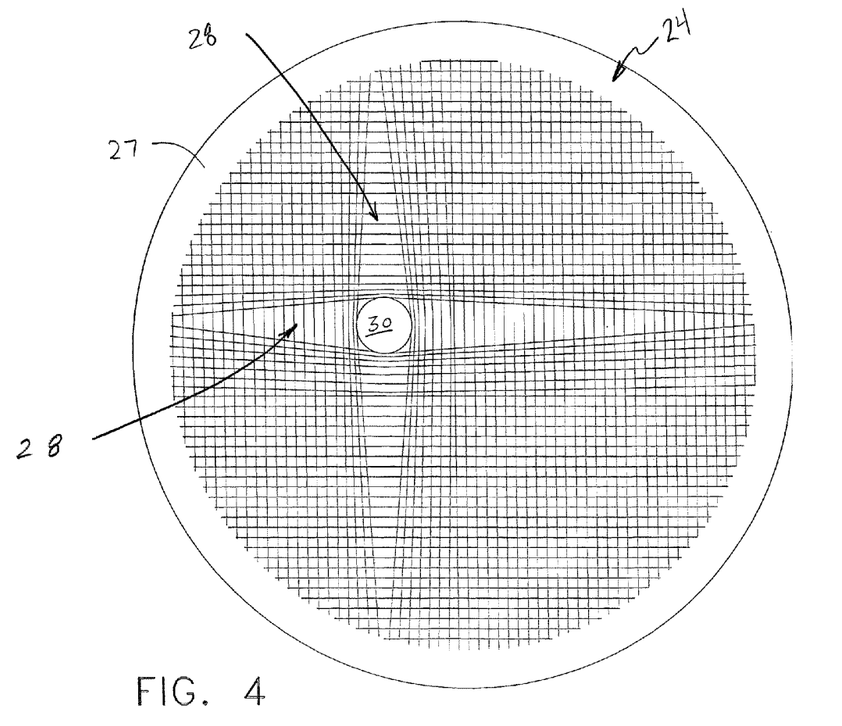
FIG. 4 illustrates a multilayered seal displaced by a surgical instrument.

When an object (30) such as a surgical instrument is placed through the seal (24), the slits (28) dilate open. The membranes (26) resiliently seal against the object (30) and by virtue of the plurality of layers provide a tortuous path preventing insufflatory fluids from escaping from the surgical site through the seal (24). When the object (30) is removed, the slits (28) return to their closed position and by virtue of the plurality of layers provide a tortuous path preventing insufflatory fluids from escaping from the surgical site. Thus, one or more objects (30) may be inserted and removed in multiple locations in the seal (24) to perform surgery while maintaining pneumoperitoneum. While some insufflatory fluids may escape through the seal (24), the tortuous path provides sufficient resistance to maintain pneumoperitoneum. Optionally, lubricants such as silicone oils or fluids, paraffin oils, water based lubricants such as polyethylene glycol and the like, may be added between the membranes (26) to reduce frictional drag as objects (30) pass through the seal (24). Friction may also be reduced by adding low friction coatings such as parylene or by chemically treatments such as chlorination.

Figure 5:
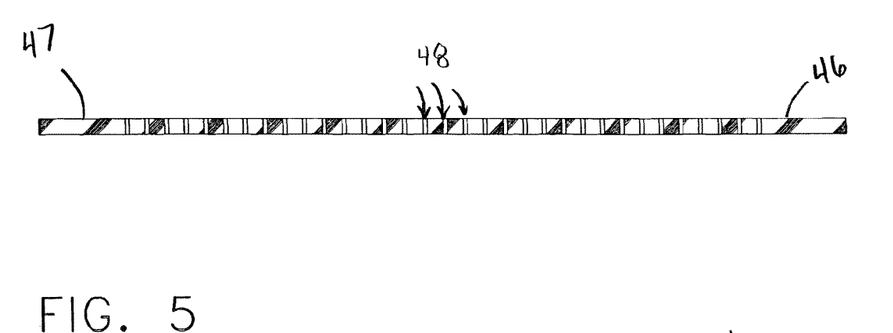
FIG. 5 depicts a cross-sectional view of a seal layer.
Figure 6:
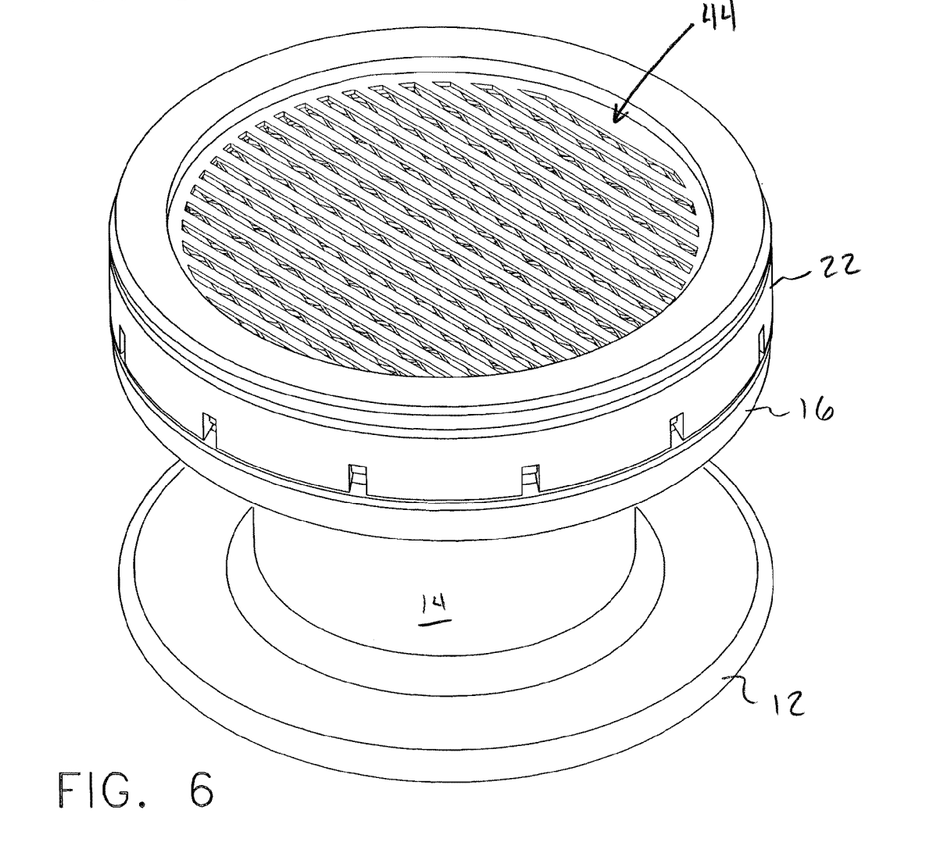
FIG. 6 depicts a perspective view of the access device with the seal layers of FIG. 5.
Figure 7:
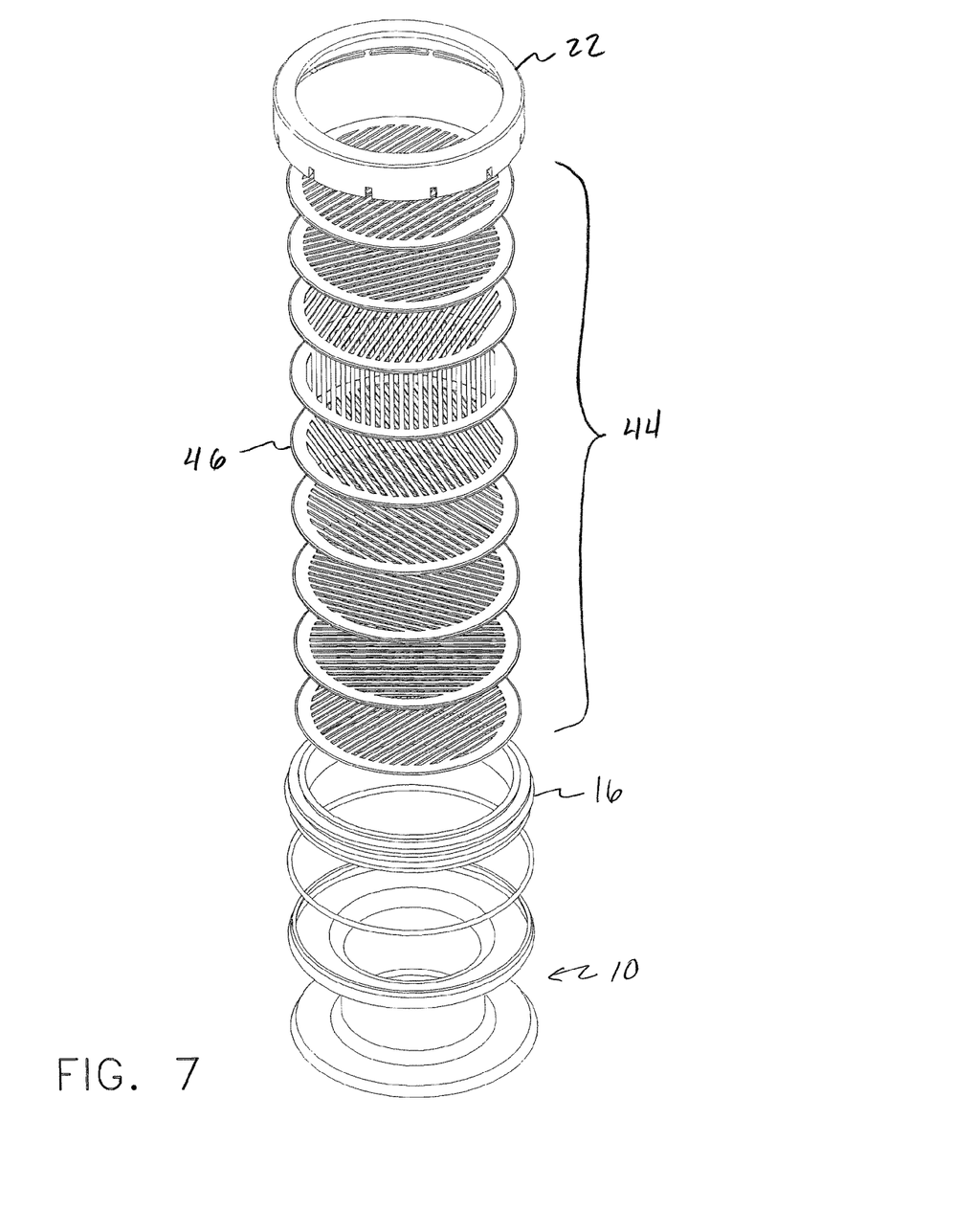
FIG. 7 depicts an exploded view of the access device of FIG. 6.

FIGS. 5-7 illustrate another example of a surgical access device. The seal (44) includes a plurality of substantially flat circular membranes (46) each having a continuous periphery (47) circumscribing a plurality of parallel slits (48). When the membrane (46) is in its resting position the slits (48) have an opening. Without limitation, the slit (48) opening widths may be between about 0.1 mm and about 2 mm. The membranes (46) are stacked upon one another such that the slits (48) of a given membrane (46) are oblique to the slits (48) of the adjacent membranes (46). Without limitation, the oblique angle may be between about 5 degrees and about 85 degrees, and more preferably between about 5 degrees and about 45 degrees.

Figure 8:
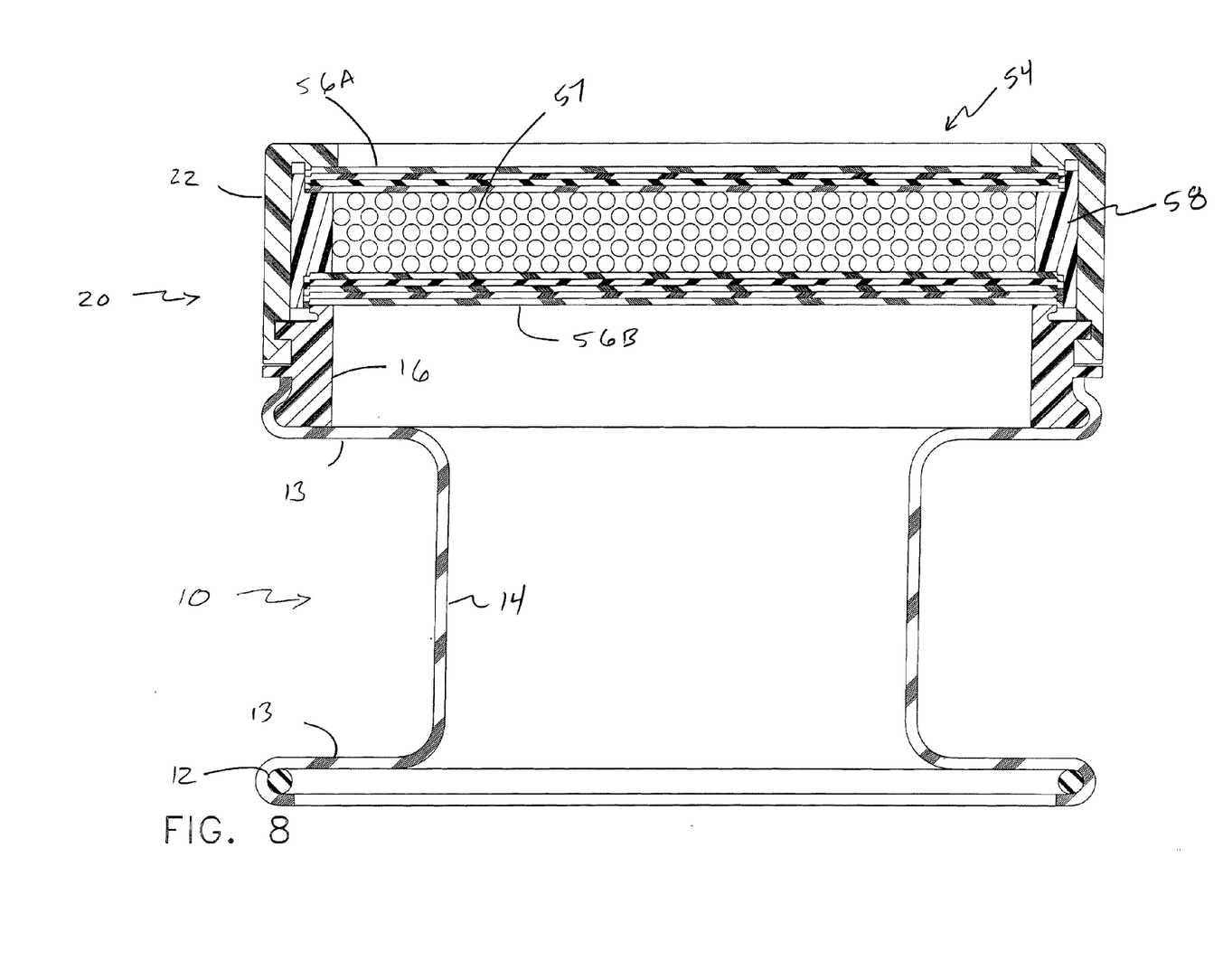
FIG. 8 depicts an cross-sectional view of an access device with a multilayered seal.
Figure 14:
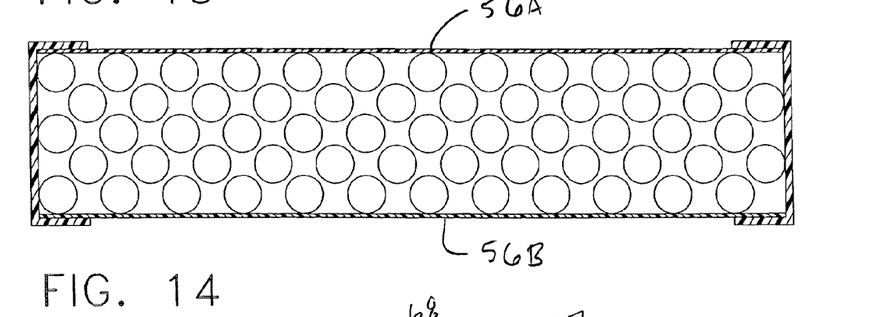
FIG. 14 depicts a plan view of a seal layer.
Figure 15:
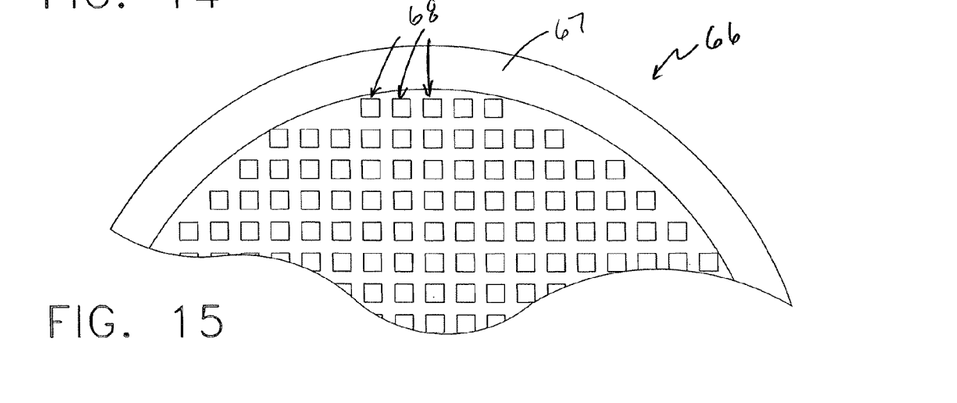
FIG. 15 depicts an cross-sectional view of an access device with a multilayered seal.
Figure 17:
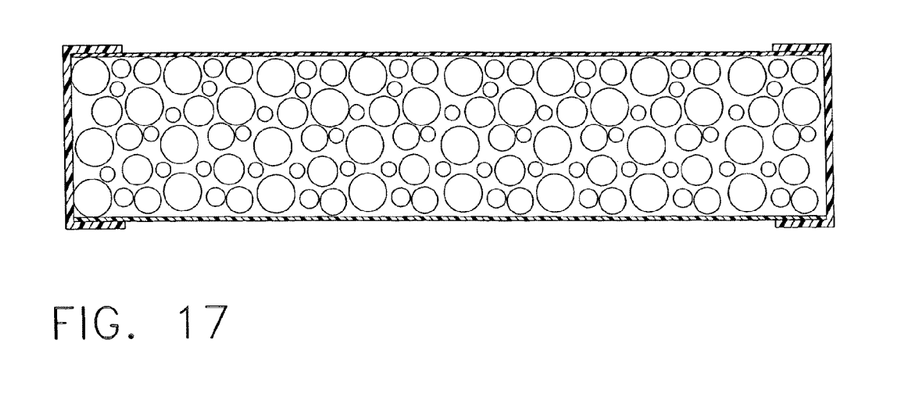
FIG. 17 depicts a cross-sectional view of an access device with a multilayered seal.

FIG. 8 illustrates another example of a surgical access device. The seal (54) includes a one or more proximal membranes (56A) and one or more distal membranes (56B), which may be similar to the membranes (26, 46) of the prior examples. A ring spacer (58) is interposed between the proximal and distal membranes (56A, B) and facilitates compressive fixation of the membranes (56A, B) between the proximal ring (16) and the retaining ring (22). The ring spacer (58) also defines a gap (57) between the proximal and distal membranes (56A, B). The gap (57) contains a plurality of loose beads made of one or more materials, including without limitation silicone elastomers (rigid or flexible), polyurethane (rigid or flexible), nylon, polyolefins, polycarbonate, polyesters, polystyrene, and foamed or porous material such as foamed polyethylene, polypropylene, polystyrene and the like. In this example the beads are spherical and are substantially the same size. Preferably the beads are sized so as not to easily escape through the membranes (56A, B). Without limitation, the volumetric displacement of each bead may range from about 0.5 $mm^3$ to about 25 $mm^3$. The beads facilitate in creating a tortuous path preventing insufflatory gases from escaping through the seal (54). In an alternative embodiment, such as illustrated in FIG. 17, the beads may vary in size. In yet another embodiment, the beads may take a variety of non-spherical geometries. FIG. 14 illustrates a variation of a seal (54) having a single proximal membrane (56A) and a single distal membrane (56B).

Figure 9:
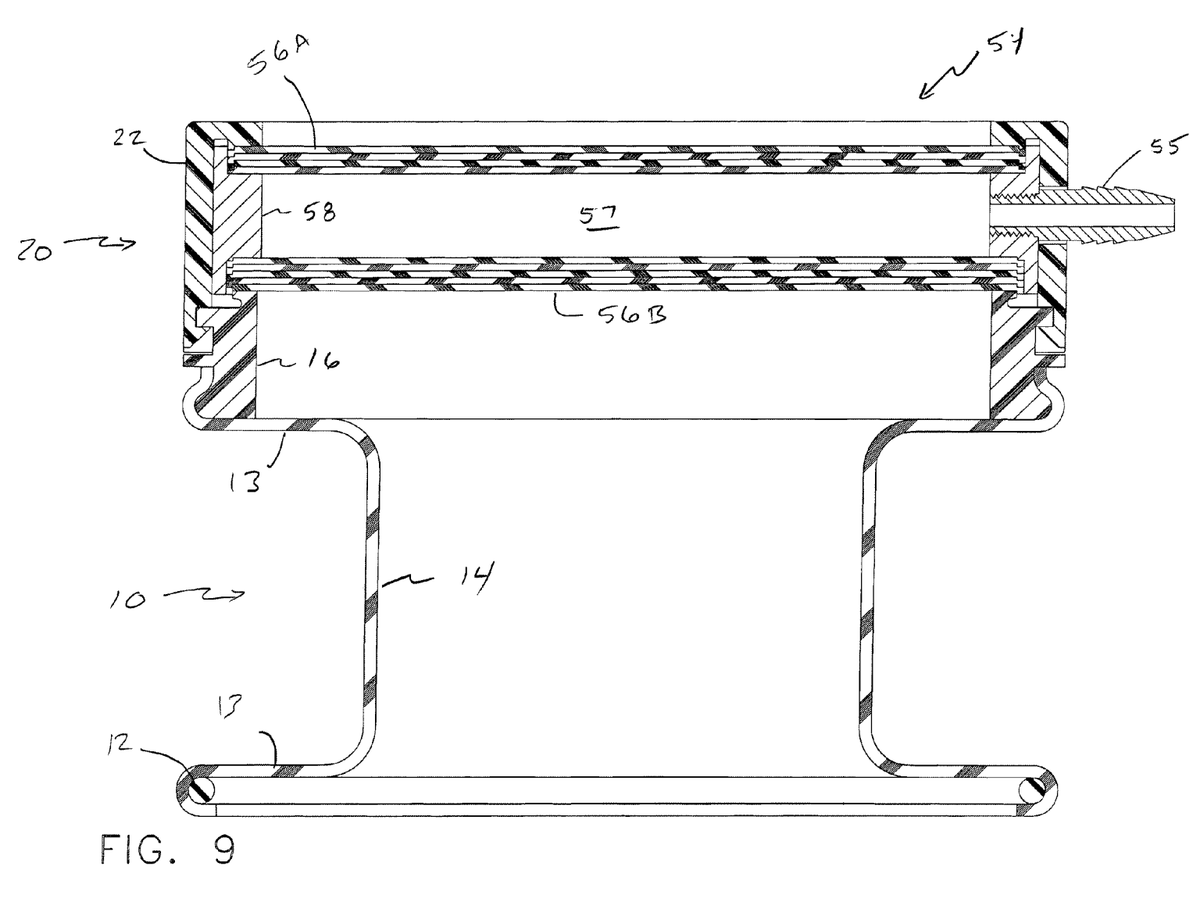
FIG. 9 depicts an cross-sectional view of an access device with a multilayered seal.

FIG. 9 illustrates yet another example of a surgical access device. Unlike the prior example, the gap (57) is filled with a fluid. The fluid may be a liquid or gas. For instance, the fluid may be pressurized carbon dioxide provided through the port (55) to minimize or eliminate a positive pressure differential across the distal membrane (56B) from the insufflated body cavity to the gap (57).

Figure 10:
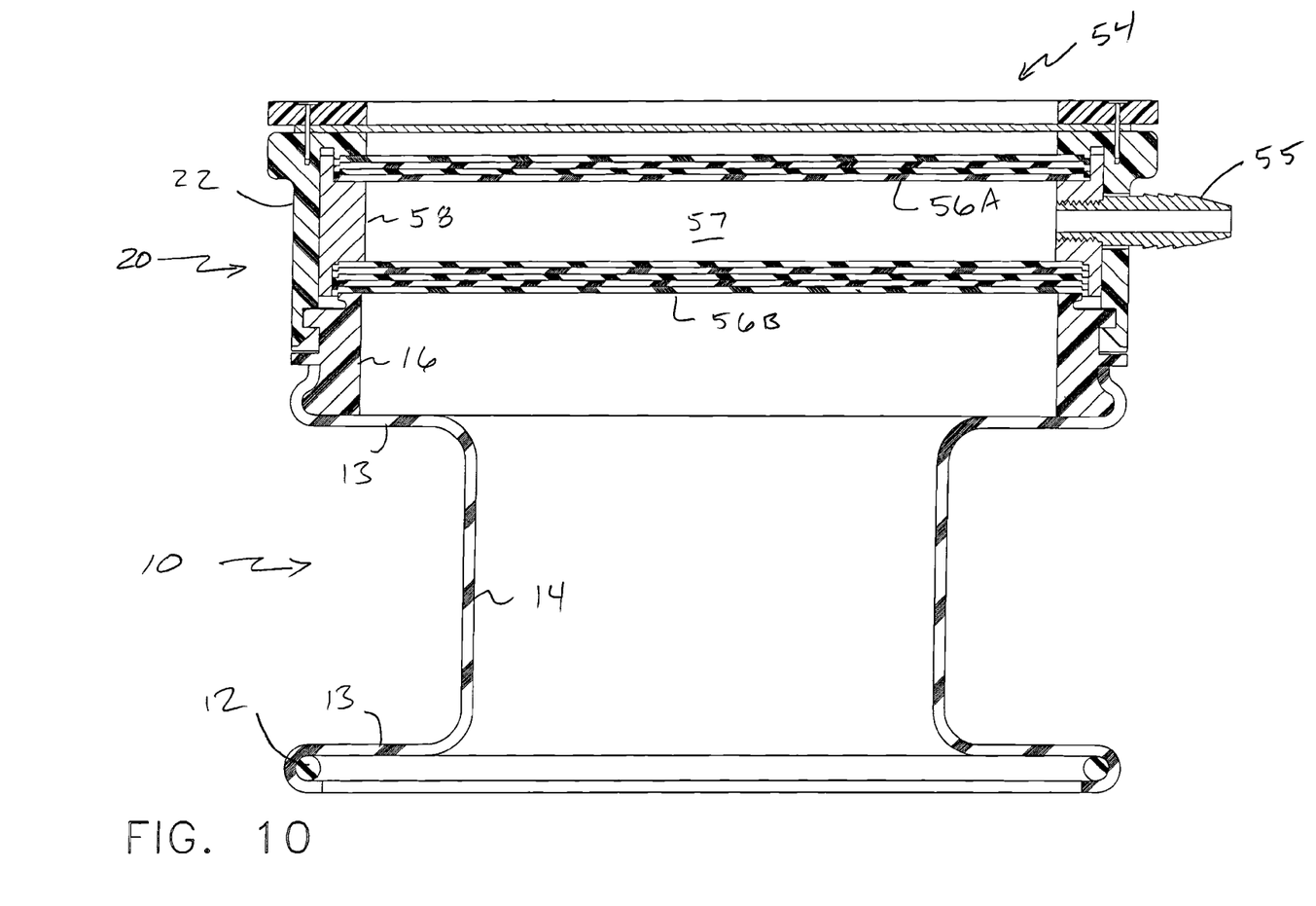
FIG. 10 depicts a cross-sectional view of a seal layer.
Figure 11:
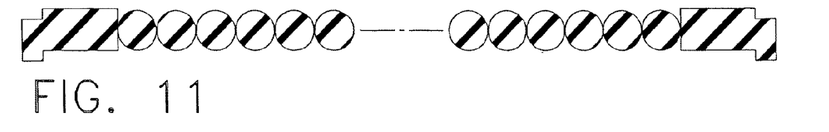
FIG. 11 depicts a cross-sectional view of a seal layer.
Figure 12:
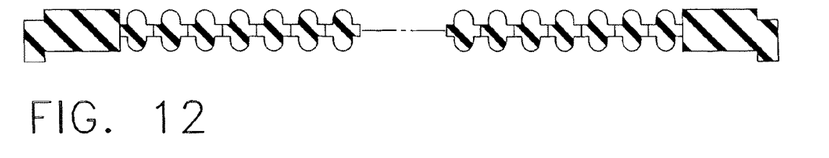
FIG. 12 depicts a cross-sectional view of a seal layer.
Figure 13:
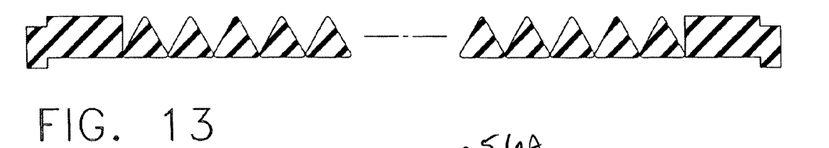
FIG. 13 depicts a cross-sectional view of a multilayered seal.

FIGS. 10-12 illustrate alternative membrane options. Instead of the flat membranes in the prior examples with rectangular cross-sectional geometries between slits, these alterative membranes include non-rectangular geometries, including without limitation circular, irregular oval, triangular, and the like.

FIG. 14 illustrates yet another alternative membrane option. The membrane (66) includes a continuous periphery (67) circumscribing a plurality of non-elongate apertures (68). In this example the apertures (68) are square, but alternative geometries are also contemplate such as circular, rectangular, triangular, and the like. Without limitation, the aperture opening may be about 0.5 $mm^2$ to about 10 $mm^2$.

Preferably, the devices described above will be processed before surgery. First, a new or used device is obtained and if necessary cleaned. The device can then be sterilized. In one sterilization technique the access device is placed in a closed and sealed container, such as a plastic or TYVEK bag. Optionally, the device can be bundled in the container as a kit with other components, including one or more of the following: a wound protector, access port, a tube of lubricant, a marker, an incision template or scale, an instruction sheet, and the like. The container and device, as well as any other components, are then placed in a field of radiation that can penetrate the container, such as gamma radiation, x-rays, or high-energy electrons. The radiation kills bacteria on the device and in the container. The sterilized device can then be stored in the sterile container. The sealed container keeps the device sterile until it is opened in the medical facility.

Having shown and described various embodiments and examples of the present invention, further adaptations of the methods and devices described herein can be accomplished by appropriate modifications by one of ordinary skill in the art without departing from the scope of the present invention. Several of such potential modifications have been mentioned, and others will be apparent to those skilled in the art. For instance, the specific materials, dimensions, and the scale of drawings will be understood to be non-limiting examples. In addition, the foregoing teachings could be implemented for HALS procedures. Accordingly, the scope of the present invention should be considered in terms of the following claims and is understood not to be limited to the details of structure, materials, or acts shown and described in the specification and drawings.

The invention claimed is:
1. A surgical access device, comprising:
   a) a wound protector;
   b) an instrument seal attached to the wound protector, the instrument seal comprising a plurality of resilient membranes each having a plurality of elongate parallel slits, the membranes being stacked upon one another such that the slits of a given membrane are oblique to the slits of the adjacent membranes to create a tortuous path preventing insufflatory gases from escaping through the instrument seal.
2. The surgical access of device of claim 1, wherein the wound protector comprises a flexible sleeve extending between a proximal ring and distal ring.

3. The surgical access device of claim 1, wherein the membranes are substantially flat and circular with a continuous periphery circumscribing the plurality of parallel slits.

4. The surgical access device of claim 1, wherein the slits have an opening width in a resting state.

5. The surgical access device of claim 1, wherein the membranes have an area between about 10 cm$^2$ and about 50 cm$^2$.

6. The surgical access device of claim 1, wherein each membrane has at least 10 slits.

7. The surgical access device of claim 1, wherein the membranes are spaced from one another to define a gap therebetween.

8. The surgical access device of claim 7, further comprising a plurality of beads positioned in the gap.

9. The surgical access device of claim 7, further comprising a pressurized fluid in the gap.

10. The surgical access device of claim 9, wherein the pressurized fluid is carbon dioxide and the gaseous pressure is equal to or greater than the pressure of the insufflatory gas.

11. The surgical access device of claim 1, wherein the device is sized to receive a surgeon's arm.

12. A surgical access device, comprising:
a) a wound protector;
b) an instrument seal attached to the wound protector, the instrument seal comprising a plurality of substantially flat and circular resilient membranes each having a continuous periphery circumscribing the at least 10 parallel slits, the membranes being stacked and compressed upon one another such that the slits of a given membrane are not parallel to the slits of the adjacent membranes to create a tortuous path preventing insufflatory gases from escaping through the instrument seal.

13. The surgical access device of claim 12, wherein the area circumscribed by the periphery is between about 10 cm$^2$ and about 50 cm$^2$.

14. A surgical access device, comprising:
a) a wound protector;
b) an instrument seal attached to the wound protector, the instrument seal comprising one or more proximal resilient membranes and one or more distal resilient membranes, the one or more proximal and distal membranes being substantially flat and circular and having a continuous periphery circumscribing a plurality of parallel slits, the one or more proximal and distal membranes being spaced from one another to define a gap.

15. The surgical access device of claim 14, further comprising a plurality of beads positioned in the gap.

16. The surgical access device of claim 14, wherein the gap contains a pressurized carbon dioxide.

* * * * *